US009730887B2

(12) United States Patent
Ragg

(10) Patent No.: US 9,730,887 B2
(45) Date of Patent: Aug. 15, 2017

(54) HYALURONIC ACID AND ITS USE FOR TREATING VENOUS INSUFFICIENCY AND VARICOSE VEINS

(71) Applicant: ANGIOCLINIC AG, Frauenfeld (CH)

(72) Inventor: Johann Christof Ragg, Berlin (DE)

(73) Assignee: Angioclinic AG, Frauenfeld (CH)

( * ) Notice: Subject to any disclaimer, the term of this patent is extended or adjusted under 35 U.S.C. 154(b) by 0 days.

(21) Appl. No.: 14/367,069

(22) PCT Filed: Dec. 20, 2012

(86) PCT No.: PCT/EP2012/076379
§ 371 (c)(1),
(2) Date: Jun. 19, 2014

(87) PCT Pub. No.: WO2013/092860
PCT Pub. Date: Jun. 27, 2013

(65) Prior Publication Data
US 2014/0378411 A1    Dec. 25, 2014

(30) Foreign Application Priority Data

Dec. 20, 2011   (EP) ..................................... 11194672

(51) Int. Cl.
| | |
|---|---|
| *A61K 31/728* | (2006.01) |
| *A61B 17/12* | (2006.01) |
| *A61K 9/00* | (2006.01) |
| *A61K 45/06* | (2006.01) |
| *A61K 31/167* | (2006.01) |
| *A61K 31/445* | (2006.01) |
| *A61K 31/485* | (2006.01) |
| *A61M 25/00* | (2006.01) |
| *A61M 25/06* | (2006.01) |
| *A61K 31/4458* | (2006.01) |
| *A61M 5/158* | (2006.01) |
| *A61B 17/00* | (2006.01) |

(52) U.S. Cl.
CPC ............ *A61K 9/0019* (2013.01); *A61B 17/12* (2013.01); *A61K 31/167* (2013.01); *A61K 31/445* (2013.01); *A61K 31/4458* (2013.01); *A61K 31/485* (2013.01); *A61K 31/728* (2013.01); *A61K 45/06* (2013.01); *A61M 5/158* (2013.01); *A61M 25/0068* (2013.01); *A61M 25/0606* (2013.01); *A61B 2017/00778* (2013.01); *A61B 2017/00783* (2013.01); *A61M 25/0693* (2013.01); *A61M 2025/0042* (2013.01)

(58) Field of Classification Search
None
See application file for complete search history.

(56) References Cited

U.S. PATENT DOCUMENTS

| | | | |
|---|---|---|---|
| 2005/0234012 A1* | 10/2005 | Jafari ................... | A61K 9/0048 514/54 |
| 2006/0052823 A1* | 3/2006 | Mirizzi ............ | A61B 17/12022 606/214 |
| 2006/0116548 A1* | 6/2006 | Case ..................... | A61F 2/2475 600/37 |
| 2007/0059350 A1 | 3/2007 | Kennedy | |
| 2007/0224278 A1 | 9/2007 | Lyons | |
| 2008/0050436 A1* | 2/2008 | Chu ..................... | A61K 9/0019 424/488 |

FOREIGN PATENT DOCUMENTS

| | | |
|---|---|---|
| CN | 1678365 A | 10/2005 |
| WO | WO 2005/037138 | 4/2005 |
| WO | WO-2009/031161 A1 | 3/2009 |
| WO | WO 2010/118435 | 10/2010 |
| WO | WO-2011/037912 A1 | 3/2011 |

OTHER PUBLICATIONS

Takashi, Yamaki et al.: "Comparative Study of Duplex-Guided Foam Sclerotherapy and Duplex-Guided Liquid Sclerotherapy for the Treatment of Superficial Venous Insufficiency", Dermatologic Surgery, vol. 30(5), pp. 718-722, May 1, 2004.
International Search Report issued on Oct. 14, 2013 in International Petent Application No. PCT/EP2012/076379.
First Office Action issued by the State Intellectual Property Office of the People's Republic of China for application CN 2012862938, filed on Dec. 20, 2012, and published as CN 2012862938 on Aug. 27, 2014 (Applicant—Angioclinic AG // Inventor—Ragg) (10 pages).
Chinese Search Report dated Dec. 19, 2016 by the State Intellectual Property Office of China for CN Application No. 201280062938.5, which was filed on Dec. 20, 2012 and published as 104010578A dated Aug. 27, 2014 (Applicant—Angioclinic AG) (Translated—3 pages).
Second Office Action dated Dec. 19, 2016 by the State Intellectual Property Office of China for CN Application No. 201280062938.5, which was filed on Dec. 20, 2012 and published as 104010578A dated Aug. 27, 2014 (Applicant—Angioclinic AG) (Original—7 pages// Translated—2 pages).

* cited by examiner

*Primary Examiner* — Leigh C Maier
(74) *Attorney, Agent, or Firm* — Ballard Spahr, LLP

(57) ABSTRACT

The present invention relates to an injectable aqueous viscous solution for treating varicose veins. It also relates to a catheter system with cannulas for vascular puncture with double or triple cut tip comprising, (i) an outer cannula (non-cutting element), a tube-like construction which is slightly flexible, (a) the tip zone being tapered to ease introduction, (b) the edges being optionally rounded to provide atraumatic advancement (c) optionally with a Luer-lock connector (ii) a hollow needle which is flexible and bendable (c) optionally with a transparent flashback chamber, wherein (d) the diameter of the needle is below the diameter of the catheter, wherein (iii) the needle and outer cannula are connected by a temporary lock to ensure the needle tip is fixed in adequate position outside the outer cannula outer cannula during skin puncture and introduction towards the target region.

10 Claims, 10 Drawing Sheets

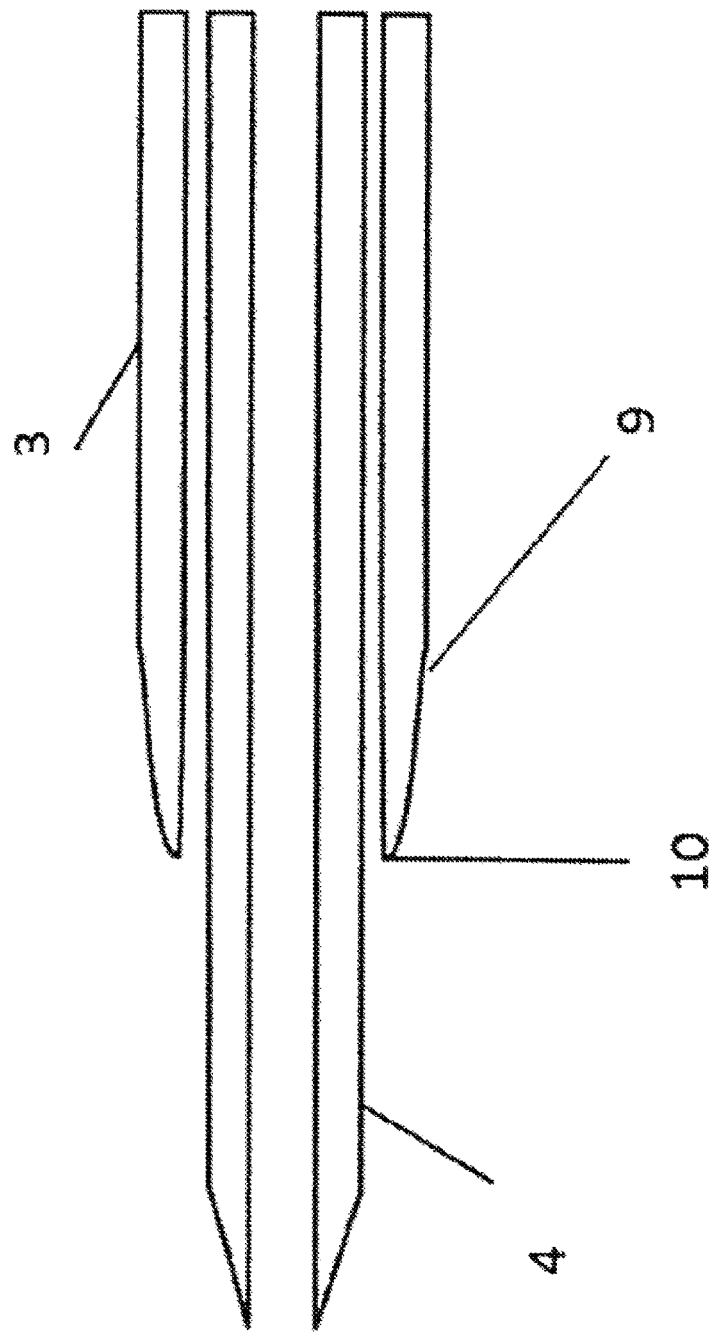

Figure 1:
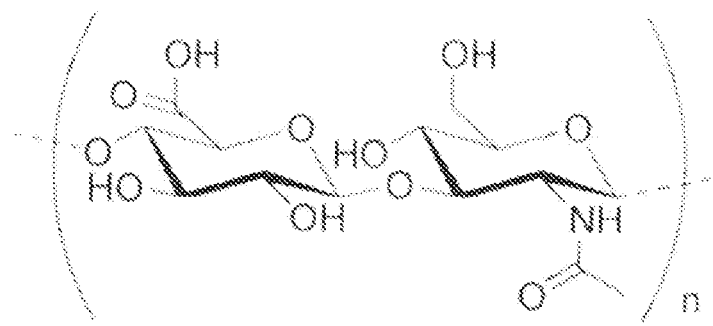

i)
ii)
iii)
iv)

ID YALURONIC ACID AND ITS USE FOR
TREATING VENOUS INSUFFICIENCY AND
VARICOSE VEINS

This application is a National Stage of PCT/EP2012/076379, filed Dec. 20, 2012, which claims priority to European Patent Application No. 11194672.9, filed Dec. 20, 2011, the disclosures of each of which are incorporated herein by reference in its entirety.

FIELD OF THE INVENTION

The present invention is in the field of medicine, more in particular in the field of vein diseases such as venous insufficiency, varicose veins, ectasias or aneurysms in humans and animals. The invention is also in the field of pharmaceuticals and medical devices for treating such diseases.

BACKGROUND

Blood vessels in humans and animals are grouped as arterial and venous, determined by whether the blood in it is flowing away from (arterial) or toward (venous) the heart.

Caused by lack of activity, an increasing number of people show venous congestion. If no change in habits occurs, congestion turns into insufficiency within few years. Insufficiency means that vein valves become incompetent, resulting in a reversed blood flow. In a vicious circle insufficiency further increases venous blood congestion, and the disease increases with time. Varicose veins are superficial veins which have been stressed by an overload of blood for years and therefore show large diameters and a tortuous course. Incompetent veins are found in 21-25% of people aged 35 or above, and spider veins even in 50% (Uldis Maurins, Barbara H. Hoffmann, Christian Liisch, Karl-Heinz jockel, Eberhard Rabe, Felicitas Pannier: Distribution and prevalence of reflux in the superficial and deep venous system in the general population—results from the Bonn Vein Study, Germany. Journal of Vascular Surgery, Vol 48, Issue 3, September 2008, 680-687)

Beside the cosmetic issues, insufficient and varicose veins lead to major complications, due to the congestion and the poor circulation through the affected limb. The complications comprise pain, heaviness, inability to walk or stand for long hours, skin inflammation, skin damage predisposing skin loss or skin ulcers especially near the ankle, usually referred to as venous ulcers, severe bleeding from minor trauma, blood clotting within affected veins (thrombophlebitis, thrombosis, embolic events). Even the development of carcinoma or sarcoma in longstanding venous ulcers has been reported in over 100 cases. The rate of malignant transformation is reported as 0.4% to 1% (Goldman M. Sclerotherapy, Treatment of Varicose and Telangiectatic Leg Veins. Hardcover Text, 2nd Ed, 1995).

For dilated veins, surgical removal of the target structure, e.g. varicose veins, is a widely used therapy. However, like all surgical treatments this may be accompanied by several, partially serious adverse effects, i.e. damaging of adjacent arteries, nerves or lymphatic vessels, generation of wounds and cicatrices, wound infections, or intolerance of the patient for narcotic drugs.

As an alternative to surgical removal, different ways of sclerotherapy have been developed.

The aim of a sclerotherapy is the permanent closure of the treated vein or vein segment. The effect may be obtained by endovascular thermal treatment (e.g. by laser, radiofrequency, steam), or by injection of chemical agents (fluids, foams). Due to the use of catheters and probes, thermal treatment is restricted to relatively linear vessels while chemical agents may also reach curved segments.

The effect of all these methods is to denature functional proteins in the innermost tissue layer (the endothelial cell layer). Effects may even reach the muscle layer of the vein. Said denaturing process triggers a shrinking of the tissue resulting in the occlusion of the target structure. Only parts of the vessel wall sufficiently reached by the sclerotic agent can be expected to close permanently, as undamaged endothelium will revitalize and lead to recurrent pathologic blood flow.

All sclerotherapy procedures are more or less associated with a local vein spasm, due to effects on the muscular layer. The spasm in general is not lasting longer than minutes above the activity of the modality, although it would be desirable to maintain it in the aim to normalize the vessel diameter. A real initial shrinking can only be obtained if the effect reaches deep into the muscular layer. On the other hand, with increasing effects on the muscular layer the danger of perforation increases, and so does pain during and after treatment.

Known liquid sclerosant drugs are e.g. alcohols with detergent properties like polidocanol or sodium tetradecyl sulphate. The liquid sclerosant drug is injected into the vessels. Due to its high fluidity the liquid sclerosant drug flows with the blood stream and quickly mixes with blood, soon reaching ineffective dilutions. Protein bindings additionally limit the effect of these fluid agents.

In order to circumvent some drawbacks of the liquid sclerosant drugs, it has been established to produce a sclerosant drug foam by mixing the liquid sclerosant drug with a gas. The resulting sclerosant drug foam is injected into the target structure, e.g. the varicose vein. For foaming the sclerosant drug (e.g. Sodium Tetradecyl Sulfate or polidocanol) is mixed with sterile air or a physiological gas (carbon dioxide) in a syringe or by using mechanical pumps.

Foaming increases the surface area of the drug. Due its higher stiffness and viscosity, the sclerosant drug foam is more efficacious in causing sclerosis than the liquid sclerosant drug (thickening of the vessel wall and sealing off the blood flow; Yamaki T, Nozaki M, Iwasaka S (2004). "Comparative study of duplex-guided foam sclerotherapy and duplex-guided liquid sclerotherapy for the treatment of superficial venous insufficiency", Dermatol Surg 30 (5): 718-22) for it does not mix with the blood in the vessel and in fact displaces it. However, sclerosant drug foams of prior art are still disintegrated rapidly within vessels. The sclerosant drug is therefore washed away from the target structure. Hence, sclerosant drug foams of prior art are not well suited for treatment of larger target structures, as they only cause painful inflammatory reactions without long lasting achievements with respect to the occlusion of the target structures. Furthermore, the sclerosant drug foams of prior art have a significant lower density than blood. This results in floating of the sclerosant drug foam on the blood within the vessels. Hence, the sclerosant drug often does not reach all portions of the vessel within the target structure.

Once a vessel disease has been treated as outlined above, the vascular dilatation or aneurysm may remain as a space consuming structure. Pressure on the neighboring nerves, vessels or organs may still remain although the diseased vessel is occluded. The larger the diameter of the diseased vein, the higher is the risk of a relapse.

For obliteration treatment of enlarged vessels, in particular sclerosant drug foam treatment, it would be advantageous to have a substance that may be used by means of injection around the dilated or aneurysmatic vessel in order to restrict its diameter. Most substances like saline solutions have turned out to be too transient. It would also be advantageous to have a substance to compress dilated veins (or vein valve zones) for a time of days to several weeks until relaxation has restored the vein function.

Thus, the present invention solves the problem by providing an aqueous solution comprising between 0.1% and 3% hyaluronic acid, and an injection kit for paravascular application.

WO 2011/037912 relates to enhancing tissue repair. It makes use of glycosaminoglycan for platelet activation, i.e. tissue repair.

DEFINITIONS

The following definitions are provided for specific terms which are used in the following.

Herein, hyalorinic acid is used with the same meaning as hyaluronan, and hyaluronate. Herein it refers to an anionic, nonsulfated glycosaminoglycan.

Hyaluronan is found in many tissues of the body, such as skin, cartilage, and the vitreous humour. The first hyaluronan biomedical product, Healon, was developed in the 1970s and 1980s by Pharmacia, and is approved for use in eye surgery (i.e., corneal transplantation, cataract surgery, glaucoma surgery, and surgery to repair retinal detachment).

Native hyaluronan has a relatively short half-life so various manufacturing techniques in fact have been deployed to extend the length of the chain and stabilize the molecule for its use in medical applications.

The introduction of protein based cross-links, the introduction of free-radical scavenging 10 molecules such as sorbitol and minimal stabilisation of the HA chains through chemical agents e.g. NASHA stabilisation are techniques that have been used.

The FDA quickly approved Healon as a surgical device in 1980, and Healon was successfully launched.

Hyaluronan is also used to treat osteoarthritis of the knee. Such treatments, called viscosupplementation, are administered as a course of injections into the knee joint, and are believed to supplement the viscosity of the joint fluid, thereby lubricating the joint, cushioning the joint, and producing an analgetic effect. It has also been suggested that hyaluronan has positive biochemical effects on cartilage cells.

Hyaluronan may also be used postoperatively to induce tissue healing, notably after cataract surgery. Current models of wound healing propose the larger polymers of hyaluronic acid appear in the early stages of healing to physically make room for white blood cells, which mediate the immune response.

In 2007, the EMA extended its approval of Hylan GF-20 as a treatment for ankle and shoulder osteoarthritis pain.

In veterinary medicine, hyaluronan is even used as intravenous injection of 10 mg (dogs) to 40 mg (horses) for the treatment of arthritis. In human medicine, intravenous injections are not established, although no adverse effect is published. Hyaluronan is used in many products for oral intake, but the effectiveness for treating arthrosis or arthritis has not been proven.

Hyaluronan is also used in anti-adhesive products such as Hyalobarrier, widely used in pelvic and abdominal surgery to prevent postoperative adhesions.

Hyaluronan is a common ingredient in skin-care products.

In 2003, the FDA approved hyaluronan injections for filling soft tissue defects such as facial wrinkles. Restylane is a common trade name for the product. Hyaluronan injections temporarily smooth wrinkles by adding volume under the skin, with effects typically lasting for six months.

Juvederm is a bacterial hyaluronic acid injectable filler, similar to Restylane, but differing slightly in terms of effect and longevity. It is used for lip augmentation, reduction of folds and wrinkles and removal of scars. The effects of Juvederm treatments are also temporary, and costs are similar to those of Restylane.

For example, Restylane is injected under wrinkles and aging lines of the face such as the nasolabial folds (nose to mouth lines), melomental folds (sad mouth corners), "crow's feet" and forehead wrinkles (frown lines). It may also be used for filling aging-related facial hollows and "orbital troughs" (under and around the eyes), as well as for cheek volume and contouring of the chin, forehead and nose. Restylane can also be used to revitalize the skin by increasing skin elasticity structure, without the goal of adding volume, for example in the face, hands and dcolletage.

Duration depends on factors like the individual's skin type, lifestyle and age. After the initial treatment, follow-up sessions are normally recommended around every 6 to 12 months depending on the individual and the treatment. A treatment of the lips lasts about 6 months. Certain Juvederm types last 12 months.

DETAILED DESCRIPTION OF THE INVENTION

The invention relates to an aqueous injectable viscous solution, for example in the form of a fluid, gel or hydrogel. The viscous solution preferably has a half-life within human connective tissue more than 1 week. The person skilled in the art will appreciate that the half-life will depend on the whether the solution is to be used in an independent therapy or as an accompanying therapy. Hence, in some cases, the half-life is preferably greater than 1 month, more preferably, greater than 3 month, most preferably greater than 6 months or even 12 months. In other cases, the half-life is between 1 week and 3 years, preferably between 1 and 12 weeks, more preferably between 4 and 6 weeks.

The term "viscous" herein denotes a solution which can be conveniently injected through the herein described catheter into tissue but still has a certain toughness such that the composition is retained in the tissue for a long time. Preferred viscosities η range from 10 to 5000 mPa*s, preferably 20 to 5000 mPa*s, more preferably 30 to 2000 mPa*s. In another aspect, the viscosity ranges between 20 and 1000 mPa*s, between 50 and 2000 mPa*s or between 50 and 1000 mPa*s. Since the viscosity is temperature dependent, injectability should be given at working temperature, e.g. between 20° C. and 40° C.

The density of the solution is preferably similar to the density of the tissue to be treated. In most cases, the tissue will be body fat. Hence, it is preferred that the density is between 0.7 and 1.2 kg/l, more preferably between 0.0 and 1.1 kg/l, most preferably between 0.9 and 1.0 kg/l or about 0.94 kg/l.

A gel is a solid, jelly-like material that can have properties ranging from soft and weak to hard and tough. Gels are defined as a substantially dilute cross-linked system, which exhibits no flow when in the steady-state. By weight, gels are mostly liquid, yet they behave like solids due to a three-dimensional cross-linked network within the liquid. It is the crosslinks within the fluid that give a gel its structure (hardness) and contribute to stickiness (tack).

Hydrogel is a network of polymer chains that are hydrophilic, sometimes found as a colloidal gel in which water is the dispersion medium. Hydrogels are highly absorbent (they can contain over 99.9% water) natural or synthetic polymers. Hydrogels also possess a degree of flexibility very similar to natural tissue, due to their significant water content.

The solution preferably comprises one or more of the following compounds: poly lactic acid, alginate, hyaluronic acid, particularly the hyaluronic acid as disclosed herein, and body fat. Poly lactic acid, for example, has been used in cosmetic treatment of wrinkles and shown to exhibit a longer residence within the human skin than cross-linked hyaluronic acid. Body fat, for the present purpose, is crushed and filtered, or the like, so that it can be injected through thin cannula (see catheter dimensions below).

In a specific embodiment, the invention relates to an aqueous solution comprising between 0.1% and 3% hyaluronic acid, preferably between 0.25% and 2% hyaluronic acid, even more preferably between 0.5 and 1% hyaluronic acid preferably crosslinked with 1,4-butanediol diglycidyl ether (BDDE). The percent herein characterizes mass concentration, i.e. for example gram per liter.

In order to achieve a life-time as defined above or modulate the life-time, there are different methods known. For example, the solution may be combined with 2-(diethyl amino)ethyl dextrane (also known as Sephadex DEAE A25), hypromellose (hydroxypropyl methylcellulose, HPMC). Alternatively, the compound(s) in the solution may be cross-linked. The thus derived solution are preferably biocompatible and do not evoke long-term irritations or inflammations. The skilled person will appreciate that the half-life of such solution are greater than that of the solution without said modifications because degrading enzymes, such as hyaloronidases, are thereby retained from the cleavage sites within the molecules. Comparable stable properties have so-called hyper-twisted, stabilized hyaluronic acids.

In one embodiment the solution further comprises inhibiting agents. Inhibiting agents herein means agents that are capable of inhibiting the degradation of one or more compounds in the viscous solution. For example, agents which have a poly saccharide-like structure inhibit the degradation of hyaluronic acid, e.g. heparin, herbal pectines and alginic acids, all of which show gel-like properties in solution. A herbal pectine may be an apple pectin. In some cases, the ability to penetrate tissue is too weak. In this case, saponins, such as glycyrrhizic acid and glycyrrhetinic acid (aglycone), which are both contained in liquorice extract, and aescin (from horse chestnut seed extract) are more effective. This applies also for flavonoids.

Further, the solution, either in addition to or instead of an inhibiting agent, may further comprise one or more endogenous substances. In one embodiment said substance is capable of forming cross-linkages with the compound in the solution. For example, a mixture of hyaluronic acid and an endogenous substance forms cross-linkages. Such endogenous substance is preferably a substance that leads to a fibrin clot. Artificial hematomas from autologous blood may be used as such substance. However, it is preferred to use autologous blood or fractions of autologous blood (platelets, coagulation factors and/or the like). In some cases, it is convenient to use blood without erythrocytes to avoid discoloration. Particularly, for the goal of long-term venous formations (treatment of valve insufficiency) this is a cost-effective solution.

Venous insufficiency, varicose veins and other disease related to vein dilatation are nowadays preferably treated by non-surgical catheter-based occlusion methods like radiofrequency, laser, steam, sclerosant foam, or glue. Except glue, none of these methods is able to initially occlude the target vessel with the necessary diameter reduction. Glue seals the vessel by wall-to-wall contact, but in all other methods the required shrinkage will take several weeks to months. Blood will re-enter the target vein in spite of external compression mediated by bandages, stockings or locally applied compressing bodies. The more blood is contained in the vessel, the longer takes the resorption process, and the higher is the risk that the resorption will go along with inflammation and pain.

With thermo occlusion methods usually tumescent anaesthesia is applied. Tumescence means to dissolve the local tissue compound. The method has been established for liposuction, and is performed by distributing large amounts of saline with local anaesthetic and optional supplements like bicarbonate, epinephrin or corticoids added, by injection manually or with pumps in the fatty tissue. The purpose is to separate fat cells from their compound and from connective tissue to support the following suction process (Klein, J. (2000). Tumescent Technique: Tumescent Anesthesia & Microcanullar Liposuction. St. Louis, Mo.: Mosby, Inc, 2000).

Applying tumescent anaesthesia on endovenous methods means to inject larger amounts of solution (USA: 400-600 ml for 40 cm vein segment) into the connective tissue adjacent to the target vein. This helps to decrease the vein lumen during treatment, contributing to a more homogenous energy deployment, but will vanish within hours. Solutions of HAES or other larger molecules have not been sufficient, vanishing within a few days. If vein compression by fluid or gel is aimed at, it should be strictly around the target vessel, but not diffuse in a large space infiltrating all kinds of surrounding tissues. In fact, due to the large amounts of fluids, tumescent anaesthesia itself is often painful for the patient.

The present desirable compression is achieved by an agent (solution) which is injectable like a fluid, but it does not propagate into the connective tissue. This means, there is a trade-off between easy injectability (low exertion) and the tendency to propagate into connective tissue, thereby decreasing the life-time of the solution. It is preferred that the solution can be injected with a force less than 50 N. In a specific embodiment said force is 7.5 to 15 N (normal exertion), in another embodiment 15 to 50 N (high exertion). It turns out to be well visible in ultrasound imaging with a distinct signal. The half-life at the inventive concentration of hyaluronic acid is 2-8 weeks for each treatment. After 8 weeks no remainders are palpable or visible.

The inventor has astonishingly found that a special aqueous solution of hyaloronan may be used very efficiently in order to treat venous diseases. Hence, in the following the invention is detailed for hyaluronic acid. However, the disclosure applies generally to any solution as disclosed herein.

The inventors have found that different to tumescent anaesthesia, the hyaluronan solution does not diffusely infiltrate the connective tissue. The hyaluronan solution was, in patients, exactly placeable around the target vein, and sufficient vein compression could be established with very small amounts of about 1-2 ml per centimeter (40-80 ml for a 40 cm vein segment). The same is true for the viscous solution disclosed herein.

In laser treatments (wavelength: 810 nm, energy: 100 J/cm) of insufficient saphenous veins (diameter 6.2-10.8 mm; 8 cases), regression times from pre-treatment to a target diameter of 25% could be reduced from 33-98 days with tumescent anaesthesia to immediate when using a solution according to the invention.

In another ongoing pilot study, two vein aneurysms of 18 and 25 mm were normalized in diameter to 6 and 7.5 mm using 3 ml of a solution or composition according to the invention, and remained with this reduced diameter during the follow-up of 90 days.

Preferably for use in occlusive vein treatments the solution of hyaluronan has a half life at the site of injection of between 2 and 8 weeks. Hence, another way of characterizing the hyaluronic acid in the aqueous solution is by way of its half life (see also above).

The invention can also be used for a shaping of dilated, incompetent valve sections by reducing the diameter. The effect can be immediately monitored in a color-coded doppler ultrasound imaging. If a diseased vein valve is restored in the sense that backward blood flow is stopped and an onward flow established, the formerly affected vein may relax and shrink due to reduced blood load. Therefore, normal vein function may be re-established by shaping diseased valve zones. The principle has been proven in a surgical method called extraluminal valvuloplasty by implanting a perivenous cuff (B. Geier, I. Voigt, L. Barbera, B. Marpe, M. Stacker, S. El Gammal, A. Mumme: Extraluminal Valvuloplasty in Insufficiency of V. saphena magna; Phlebologie 2004, Vol. 33:5; 145-185).

The advantages of the solution or composition for the treatment outlined above are multiple: The solution is not immunogenic, biocompatible, of non-animal origin, binds water very well and body resorption is very good.

Hyaluronan (also called hyaluronic acid or hyaluronate) is an anionic, nonsulfated glycosaminoglycan distributed widely throughout connective, epithelial, and neural tissues. It is unique among glycosaminoglycans in that it is nonsulfated, forms in the plasma membrane instead of the Golgi, and can be very large, with its molecular weight often reaching the millions.

Hyaluronan is a polymer of disaccharides, themselves composed of D-glucuronic acid and DN-acetylglucosamine, linked via alternating β-1,4 and β-1,3 glycosidic bonds; see FIG. 1. Hyaluronan can be 25,000 disaccharide repeats in length. Polymers of hyaluronan can range in size from 5,000 to 20,000,000 Da in vivo. The average molecular weight in human synovial fluid is 3-4 million Da, and hyaluronan purified from human umbilical cord is 3,140,000 Da.

It is preferred that the hyaluronic acid has between 1 million and 8 million Da, more preferably between 2 and 6 Mio. Da, more preferably between 3 and 5 Mio Da. About 4 million Da is most preferred (+/−20%).

The hyaluronan is obtained by bacterial fermentation, passing sterile filtration and optional heat treatment. Additionally, potential endotoxins may be extracted. Thermal sterilization may reduce the length of molecular chains.

Hyaluronan is energetically stable, in part because of the stereochemistry of its component disaccharides. Bulky groups on each sugar molecule are in sterically favored positions, whereas the smaller hydrogens assume the less-favorable axial positions.

One preferred solution is obtained by crosslinking Hyaluronic Acid (HA) with 1,4-Butanediol Diglycidyl Ether (BDDE). Such a solution passes all the biocompatibility tests. BDDE is a sensitizer and has also found to be a mutagen in Drosophila (Foureman et al, Environ Mol Mutagen 1994; 23(1):51-63). To address the carcinogenicity potential of the residual BDDE (2 ppm) present in the device, one can cite an animal study conducted on BDDE by CIBA-GEIGY. The animal study investigators felt the study was not conclusive to say BDDE is a systemic carcinogen. Therefore, BDDE is considered to be today's least toxic cross-linking agent.

In certain embodiments the solution may additionally comprise a local anesthetic. These may be scandicain, mepivacaine, cocain, procain, benzocain (Ethoform), lidocain, mepivacain, bupivacain, ropivacain, etidocain, prilocain and tetracain but also others. Corticoids may be used to prevent perivascular inflammations. Further substances may be added to delay or accelerate the resorption of HA or the compounds in the composition.

The signal intensity of the substance can be varied from equal to water to more intense than human tissue, by adding small amounts of gas (Carbondioxid, Oxygen, air, or mixtures thereof), e.g. 1-10 vol.-%, and prepare an injectable mixture. In contrary to water-like fluids, gas bubbles will be stable for minutes to hours in hyaluronan due to its gel-like viscosity.

Normally, the desired ultrasound signal will be equal to water, as this allows the best view on the vein and the endoluminal tools, but in some indications (e.g. aneurysm) it may be preferred to use an ultrasound pattern much different from water to easier differentiate aneurysm and compressing substance.

The preferred pH of the solution is 7.2+/−0.1.

The solution may additionally comprise $CO_2$, $O_2$, air or mixtures thereof, in amounts of 1-10%.

The invention also relates to the inventive solution for use as a medicament.

Preferably the solution is used for treating dilatative or ectatic venous diseases. Hence, the invention also relates to a method of treating a patient which has venous disease. The venous disease is preferably characterized by dilated veins.

Preferably, the venous disease is select from the group of venous insufficiency, dilated veins, varicose veins, ectasias or aneurysm.

The amount of solution, e.g. hyaluronan solution, for one patient may have a volume of between 3 ml (e.g. small aneurysms) and 200 ml (e.g. long ectatic veins).

The invention also relates to a kit comprising a solution according to the features outlined above and one of the following: a hollow needle, a catheter and/or a tube. Preferably, the catheter is a catheter system as described below.

A catheter system herein is a medical device that can be inserted in the body to treat diseases, particular vein diseases. The catheter system according to the invention comprises a needle for vascular puncture with double or triple cut tip which suit the purpose of easy skin puncture and an outer cannula. The outer cannula may be most appropriately called a catheter, though catheters are usually made of rubber. In order to provide the present catheter system the material of known catheters would be in most cases too weak. Hence, the herein disclosed catheter system and the catheter (outer cannula) differs from the known ones in that they are characterized as disclosed herein. Catheters or tubes near to the required kind are known from biopsy, where they serve as outer part (non-cutting element). Needles for tumescent anesthesia in liposuction are either sharp cannulas, or tube-like tools with multiple side-holes for rapid tissue infiltration.

The catheter system according to the invention differs largely from all existing coaxial catheter or needle systems, as there so far has been no construction for the invention's purpose, i.e. to safely deploy viscous solutions around vascular structures.

Straight coaxial systems for intravascular use are widely spread and used for infusions, transfusions or to take blood samples. They consist of a hollow needle with a sharp tip penetrating tissue layers, and a second, outer tube of plastic material which remains within the vessel after the inner needle has been removed. Such plastic tubes are far too soft and vulnerable to kinkings as to use them as a steerable blunt cannula for the deployment of gels or fluids outside of vessels.

Coaxial tube systems used for biopsy usually contain an inner element which is solid to replace tissue material and leaving it for the outer tube to aspirate a sample. The purpose is to cut and collect tissue samples. There are few coaxial biopsy needle systems consisting of two sharp hollow structures. There is no biopsy system containing one blunt and one sharp, unfenenstrated tubes.

There are coaxial systems for lumbar anesthesia, but they are not straight to fit to the given anatomy. Furthermore, they are stiff to pass the resistant connective perilumbar tissue.

Cannulas for liposuction are made of metal with minimal flexibility, but are just a single tube instrument, normally with a closed end, a rounded tip and a side window near the tip for the collection of fat cells.

Finally, there are some constructions called "safety cannula" which consist of a cannula with a sharp tip for puncturing, and a device to cover this sharp tip when the cannula is withdrawn to avoid injuries. Other constructions allow the introduction and pull-back of hollow needles into a catheter, an endoscope or other tools. However, this does not refer to highly flexible coaxial injection tubes.

In contrast to the above the catheter disclosed herein comprises two coaxial straight tubes (cannulas), open at both sides, the first tube with a sharp tip, i.e. a needle, and the second tube with a blunt tip, i.e. outer part, herein also denoted outer cannula (non-cutting element). Both tubes are flexible and/or elastic. The tubes are composed at a distance allowing easy relocation but preferably no manually perceptible play when steering the tip by moving the handle. The system of both tubes is designed for advancing it to positions outside diseased vessels, to deploy viscous compositions around the vascular structures for shaping them or reducing their diameter for a time period from weeks to months (see above).

The needle is positioned within the cannula having a blunt tip. Accordingly, the needle has a smaller outer diameter than the inner diameter of the outer cannula. The needle may be supplemented by a transparent aspiration chamber to monitor incidental intravascular positions or hematoma after vascular injuries.

It is preferred that a connector element allows withdrawal of the needle into an injection position for the safe extravascular deployment of viscous compositions, and/or movement of the needle into a puncturing position in order to penetrate skin and connective tissue layers until the target position has been reached. Preferably, the cannulas can be fixed in predetermined positions relative to each other in one or both of said positions.

The puncturing position may be characterized in that the tip of the needle is 2 to 8 mm ahead of the outer cannula. The injection position may be characterized in that the tip of the needle is positioned within the outer cannula. For example, the needle may be withdrawn by some mm such that the needle is located and fixed 4 to 6 mm before the opening of the outer cannula.

Herein, sharp means that the cannula is able to penetrate skin and connective tissue, for example the force applied is less than 5, preferably less than 3 or even less than 1.5 N. Blunt means that the cannula cannot penetrate skin or connective tissue, for example when the force applied is less than 3, preferably less than 4 or even less than 5N. The person skilled in the art will appreciate that the above values depend on the outer diameter of the cannula and, thus, relate to cannulas with an outer diameter of about 0.8 to 1.2 mm. More specific, for cannulas with an outer diameter of 0.8 mm and 1.2 mm, the values for a sharp cannula may be less than about 1.5 N and less than about 2.0 N, respectively. The values for a blunt cannula may be less than about 3 N and less than about 4 N, respectively.

The needle and/or outer cannula are flexible and elastic in a way such that the catheter can both penetrate the skin at an angle of 10 to 90 degrees, preferably 20 to 45 degrees, relative to the skin surface and can be steered parallel to the vessel, which is parallel to the skin surface in most of the cases. In certain embodiments, this may mean that the coaxial tubes bent for 5 to 90 degrees, preferably 5 to 50 degrees, more preferably 5 to 30 degrees or more than 10 degrees when a bending force less than 1N is applied. In other embodiments, the cannula will bend for 10 to 40 mm, preferably 10 to 30 mm or 15 to 25 mm (measured at the tip), when the tip is stressed with a force of 0.2 N. The definition may apply to the needle and/or the outer cannula and/or to the catheter system, i.e. when both cannulas are assembled.

"Elastic" means that the tube returns to the original, straight shape, when stressing the tip of a 100 mm long cannula with a force of 0.2 N (20 g). These properties are rarely reached by some small injection needles, but not by any existing coaxial needle system.

For easy and pain-free introduction and positioning the catheter system is preferably as small as possible and does not exceed a maximum outer diameter (OD) of 3.0 mm, preferably 2.0 mm, more preferably 1.5 mm. However, for easy deployment of viscous fluids or gels, it is preferred that the inner diameter (ID) is at least 0.3, preferably 0.5 mm.

The catheter system, in a specific embodiment, has the following dimensions. The total length of the catheter is 60 to 250 mm, preferably 80 to 180 mm, more preferably 100 to 140 mm. The needle has an outer diameter (OD) of 0.6 to 0.9 mm, preferably 0.7 to 0.8 mm. Its inner diameter (ID) is 0.45 to 0.8 mm, preferably 0.6 to 0.7 mm. The needle's wall diameter (WD) is 0.05 to 0.15 mm, preferably 0.75 to 0.125 mm, more preferably 0.8 to 1.0 mm. The outer cannula's outer diameter (OD) is 0.7 to 1.2 mm, preferably 0.9 mm. The outer cannula's inner diameter (ID) is 0.6 to 0.9 mm, preferably 0.8 mm. The outer cannula's wall diameter (WD) is 0.05 to 0.15 mm, preferably 0.075 to 0.125 mm, even more preferably 0.08 to 0.1 mm.

In another specific embodiment, the catheter according to the invention comprises a tube-like construction, which preferably has an outer diameter of 0.9 to 1.2 mm, and an inner diameter of 0.8 to 1.1 mm. It is (slightly) flexible.

The person skilled in the art will appreciate that at least some of the above dimensions depend on the material of the cannulas. This is particularly true for the wall diameter. In any case, the inner diameter of the outer cannula is smaller than the outer diameter of the needle such that the cannulas can be plugged into each other (see above). The wall diameter means the thickness of the tube's wall.

It is further preferred that the radial distance between the cannulas is less than 20% of the ID of the second tube, preferably less than 15% and more preferably less than 10% to conduct any movement of the rear end to the tip without perceptible play.

The cannulas of the catheter system may be made of metal, plastic, carbon fibre and other medically accepted materials provided that these materials have the features as disclosed herein. A preferred material is metal, such as stainless steel.

In one embodiment, the tube consists of metal. In another embodiment, it consists of plastic material. The tip zone may be tapered to ease introduction. The edges may be rounded to provide atraumatic advancement. In one embodiment, it comprises a Luer-lock connector.

The hollow needle may be flexible and bendable. It may comprise a transparent flashback chamber for early indication of blood from eventual vessel puncture. The diameter of the needle is below the diameter of the outer cannula with a distance that allows easy needle removal (0.05 to 0.10 mm). The inner diameter determines the force required for injection, therefore it should not be smaller than 0.25 mm. An easy injection is performed using cannulas with an inner diameter of 0.4-0.8 mm. The needle may comprise a Luer lock connector, or another connector for the hyaluronan syringe. Needle and outer cannula are connected by a temporary lock to ensure the needle tip is fixed in adequate position outside the catheter during skin puncture and introduction towards the target region. The connection may be achieved by thread, hooks, humps, plugs, magnets, and adhesive materials or otherwise.

The catheter system kit comprises cannulas for vascular puncture with double or triple cut tip, the catheter comprises
 (i) an outer part (non-cutting element), a tube-like construction which is slightly flexible, of a metal or plastic material, preferably of 0.9 to 1.2 mm in outer diameter, and 0.8-1.1 mm inner diameter,
  (a) the tip zone being optionally tapered to ease introduction,
  (b) the edges being optionally rounded to provide atraumatic advancement
  (c) optionally with a Luer-lock connector.
 (ii) a hollow needle which is flexible and bendable
  (a) optionally with a transparent flashback chamber, wherein
  (b) the diameter of the needle is below the diameter of the catheter, wherein
 (iii) the needle and catheter are connected by a temporary lock to ensure the needle tip is fixed in adequate position outside the catheter during skin puncture and introduction towards the target region.

The system is first used in connected mode with the cannula tip in front to penetrate resistant structures (skin, fascia) until perivascular target position is reached. Extravascular position and proof of no vascular lesion is shown by aspiration: No blood should show on the flashback chamber, otherwise the position has to be changed. After positioning, the cannula is removed. Hyaluronan or another solution (see above) is injected, and the catheter moved for adequate allocation of the hyluronan. Catheter movements can be performed without risk of incidentally puncturing the target vein or other relevant vessels, or damaging nerves because of the blunt tip.

The invention also relates to a preloaded syringe, wherein the solution according to the invention has been loaded. The kit may also comprise such a syringe.

EXAMPLES

Example 1

15 ml of an aqueous solution comprising 0.5% hyaluronic acid were mixed with 2 ml of 2% solution of Scandicain and injected as shown in the figures. After 2 weeks, the compression by hyaluronan was still effective (FIGS. 14-15), while the contralateral side similarly treated by using saline was totally uncompressed.

Example 2

Regression of Vein Diameters after Sclerotherapy

Sclerotherapy of veins was conducted. Subsequently, an aqueous solution comprising 1% hyaluronic acid (not cross-linked) according to the invention (with IntraShape 1%) was administered to the tissue surrounding the treated vein. The diameter of the treated vein was determined after three time points and its reduction in percent was calculated. The results were compared to the results obtained without administering a solution or composition according to the invention (without IntraShape).

20 patients, target vein with diameter of 6 to 22 mm and length of segment to be treated 23 to 45 cm.

|  | 14 d | 30 d | 3 mon. |
|---|---|---|---|
| without IntraShape | 22.2% | 34.7% | 48.1% |
| with IntraShape 1% | 52.0% | 62.0% | 74.4% |

Example 3

Two patient groups were treated as described in example 2 and further examined with respect to the occurrence of hematoma after perivenous tumescence.

20 patients per group, great saphenous vein (GSV), diameter 8.2 to 22.1 mm.

|  | Number of patients | Visible hematoma n | Visible hematoma (%) % | Number of patients with symptoms n | Occurrence of symptoms (%) % |
|---|---|---|---|---|---|
| without IntraShape | 20 | 14 | 70.0 | 5 | 25.0 |
| with IntraShape 1% | 20 | 1 | 5.0 | 0 | 0.0 |

Example 4

Cannulas with a preferred flexibility were determined as follows. The first (sharp) cannula, the second (blunt) cannula and the catheter (both cannulas assembled), respectively, were pressed against scales. Upon bending the movement of the tip relative to its tangent and the weight was recorded (see FIG. 15). The respective force was calculated. Results are shown below and visualized in FIG. 16.

Flexibility of first cannula (OD 0.8 mm; WD 0.125 mm; length 100 mm):

| tip bent mm | weight g | force N |
|---|---|---|
| 1 | 6.2 | 0.06 |
| 2 | 11.8 | 0.12 |
| 3 | 18.2 | 0.18 |
| 4 | 24.8 | 0.24 |
| 5 | 33.2 | 0.33 |

Flexibility of second cannula (OD: 0.95 mm, WD 0.125 mm; length: 100 mm):

| tip bent mm | weight g | force N |
|---|---|---|
| 1 | 7.1 | 0.07 |
| 2 | 13.1 | 0.13 |
| 3 | 19.5 | 0.19 |
| 4 | 26.7 | 0.26 |
| 5 | 35.8 | 0.35 |

Flexibility of both cannulas:

| cannula tip bent mm | sharp weight g | blunt weight g | both weight g |
|---|---|---|---|
| 1 | 6.2 | 7.1 | 12.8 |
| 2 | 11.8 | 13.1 | 23.9 |
| 3 | 18.2 | 19.5 | 37 |
| 4 | 24.8 | 26.7 | 51.3 |
| 5 | 33.2 | 35.8 | 68.4 |

FIGURE CAPTIONS

Figure 2:
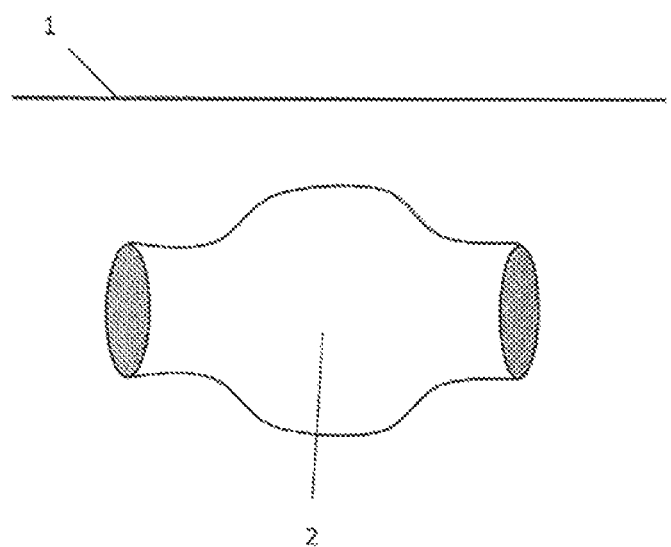
Figure 3:
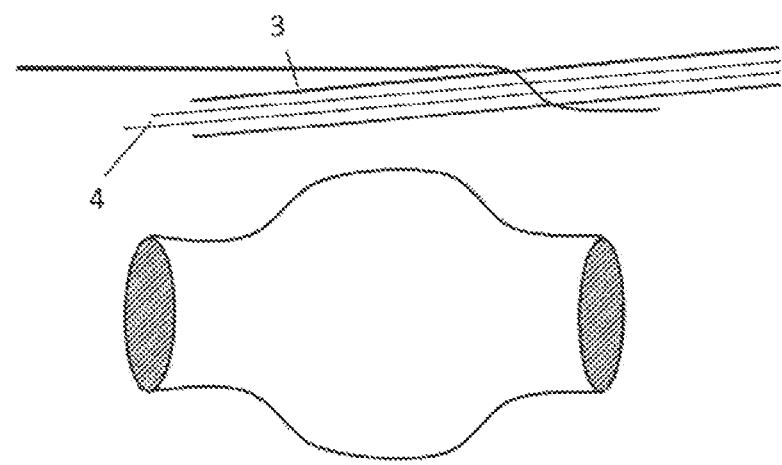
Figure 4:
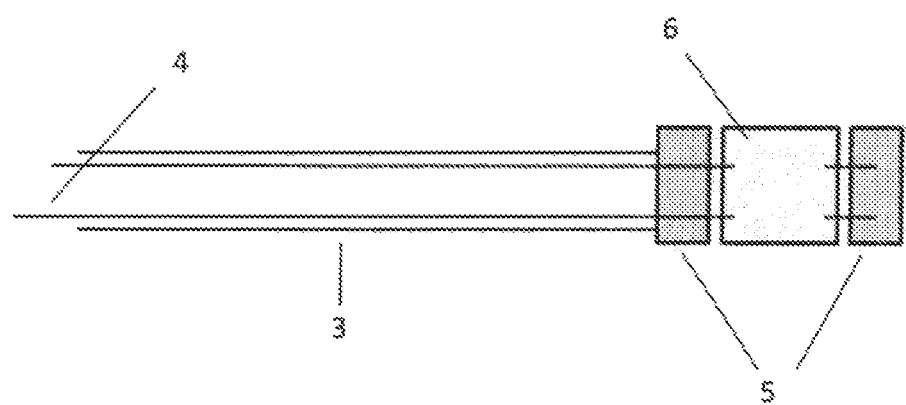
Figure 5:
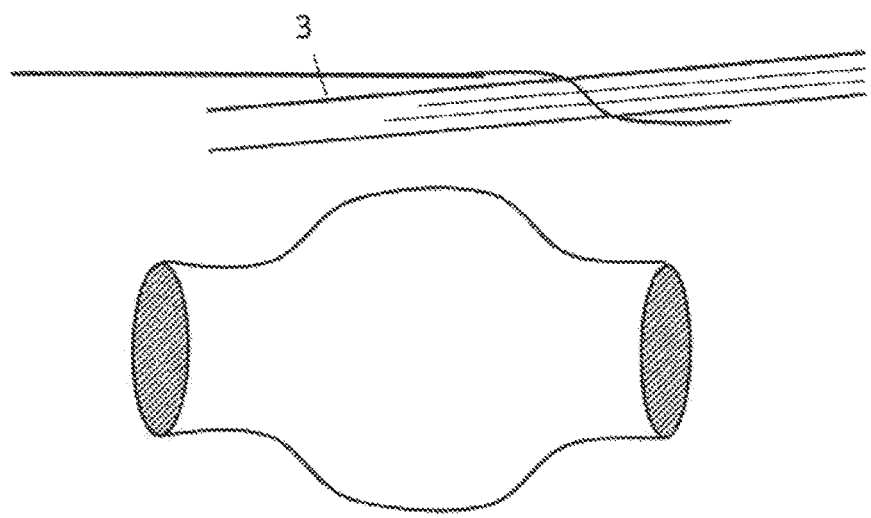
Figure 6:
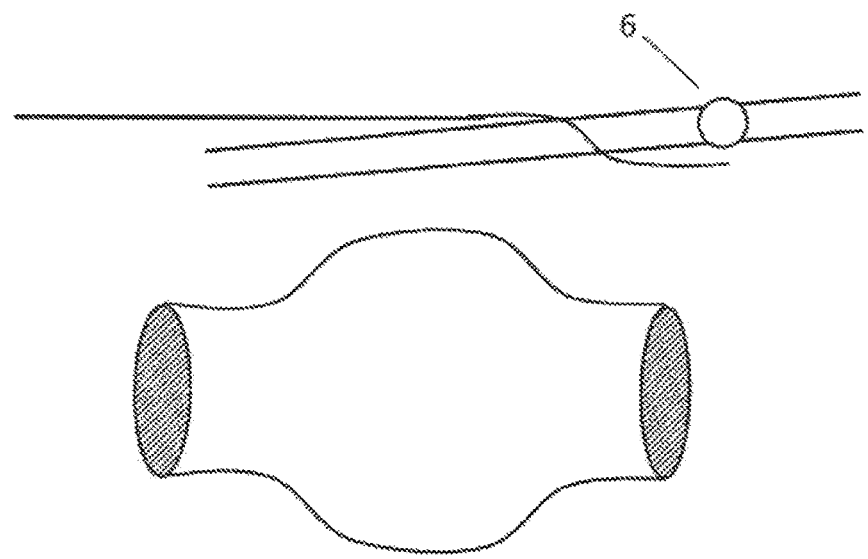
Figure 7:
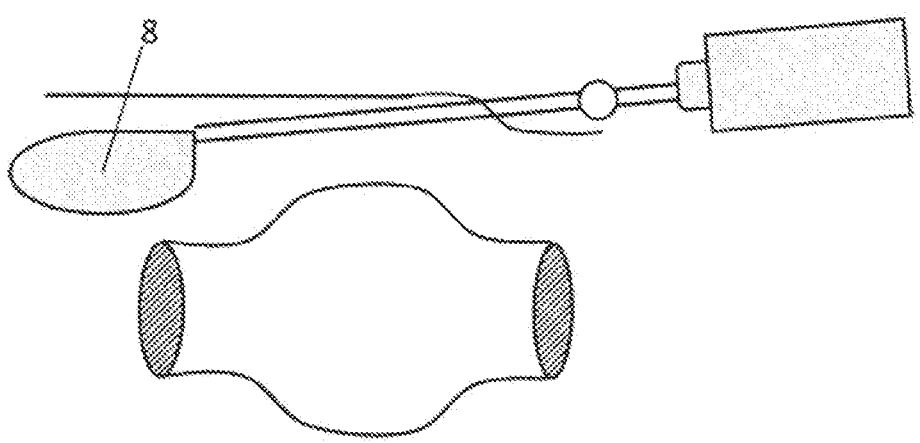
Figure 8:
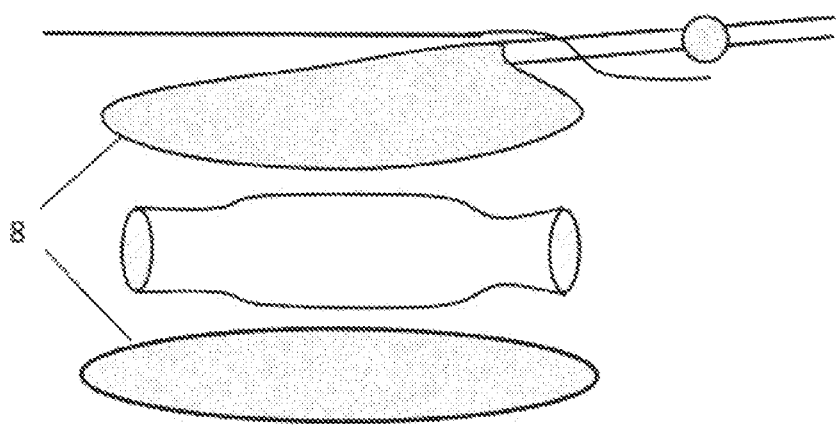
Figure 9:
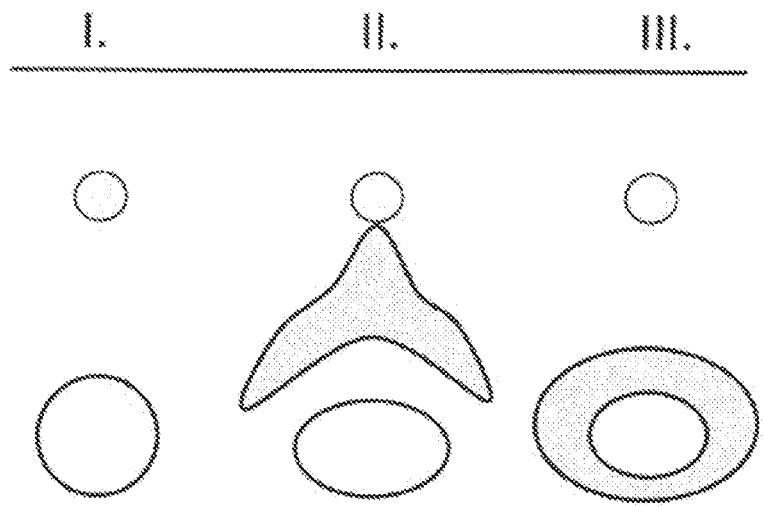
Figure 10:
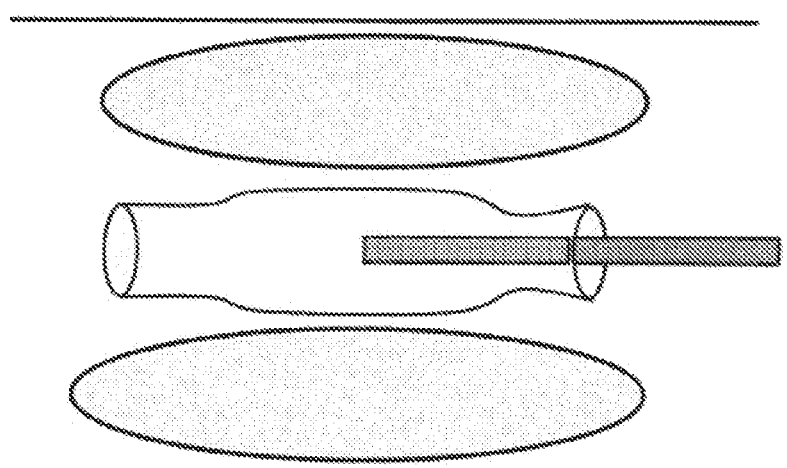
Figure 11:
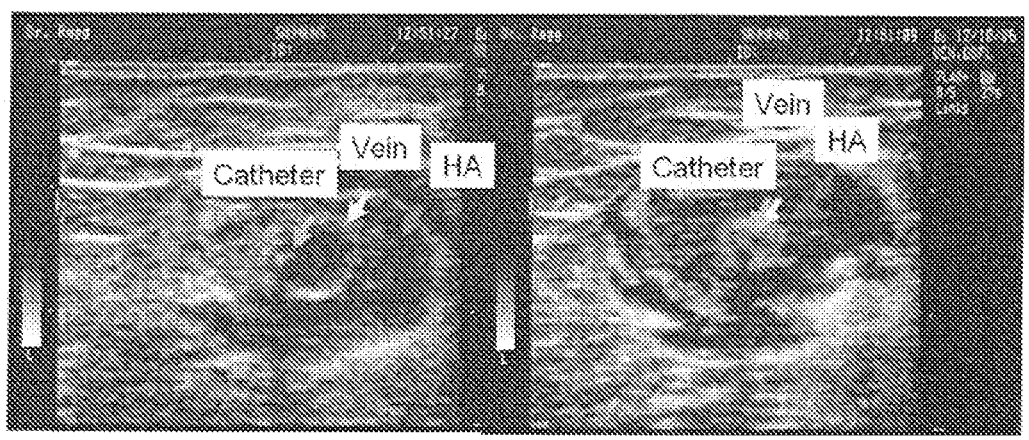
Figure 12B:
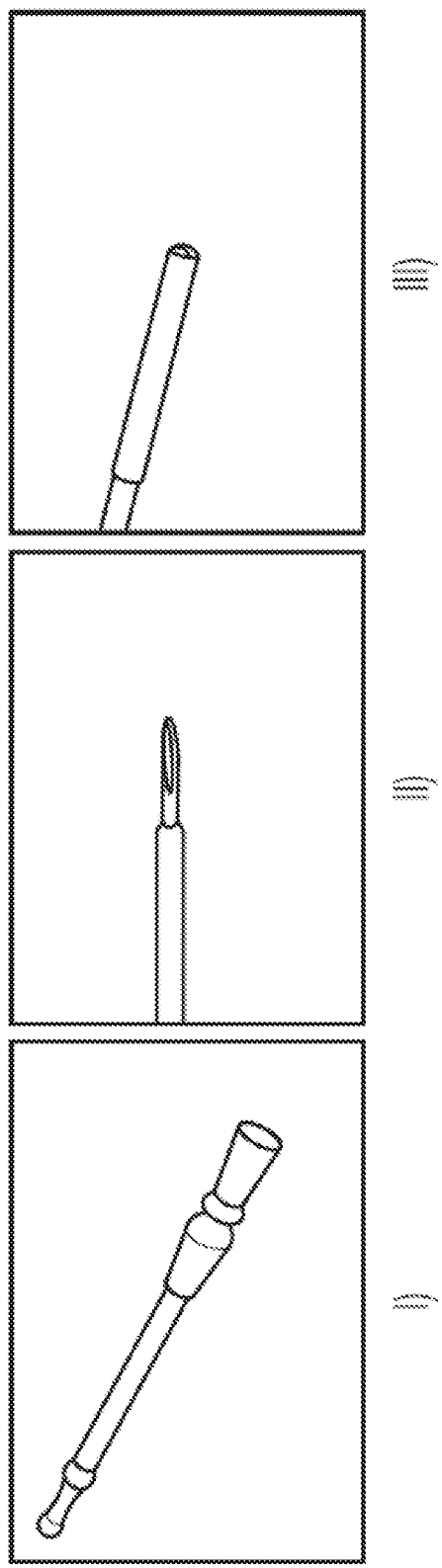
Figure 13:
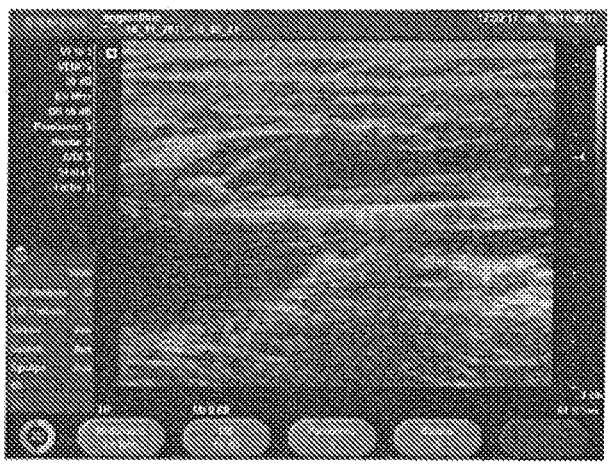
Figure 14:
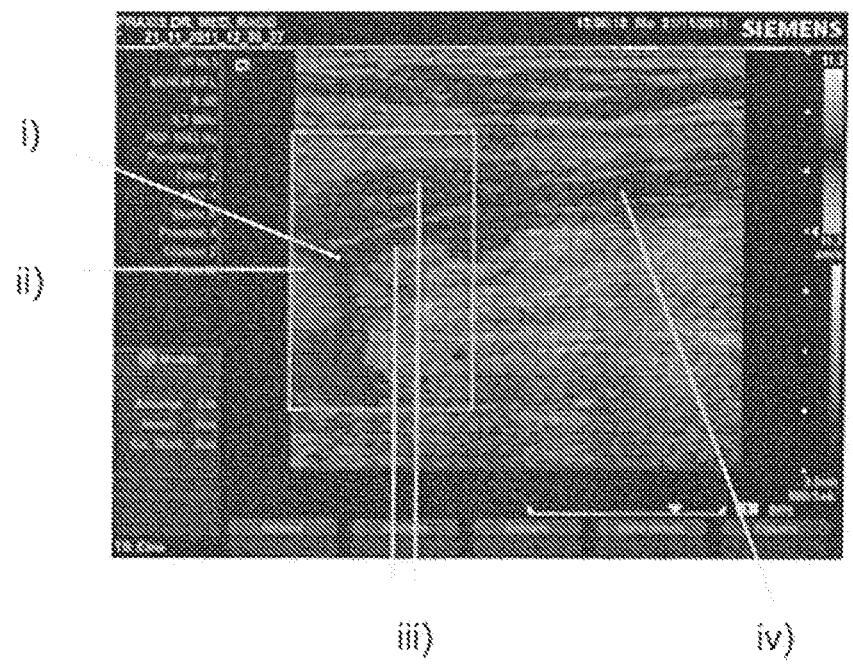
Figure 15:
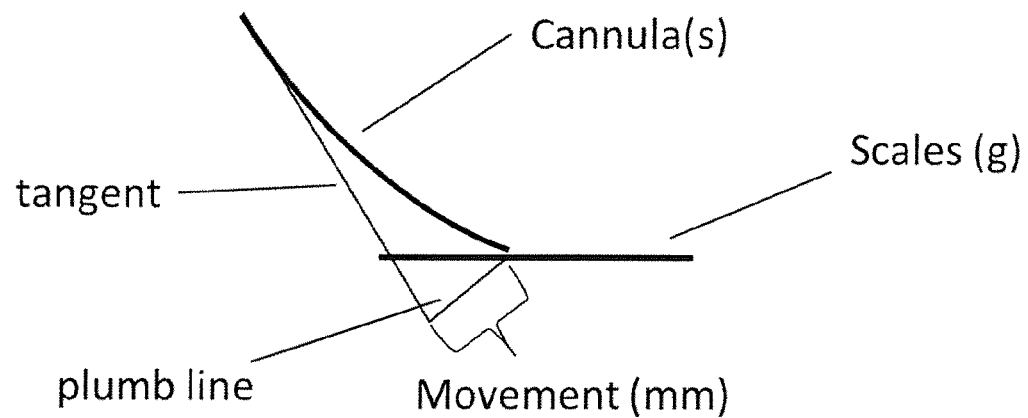
Figure 16:
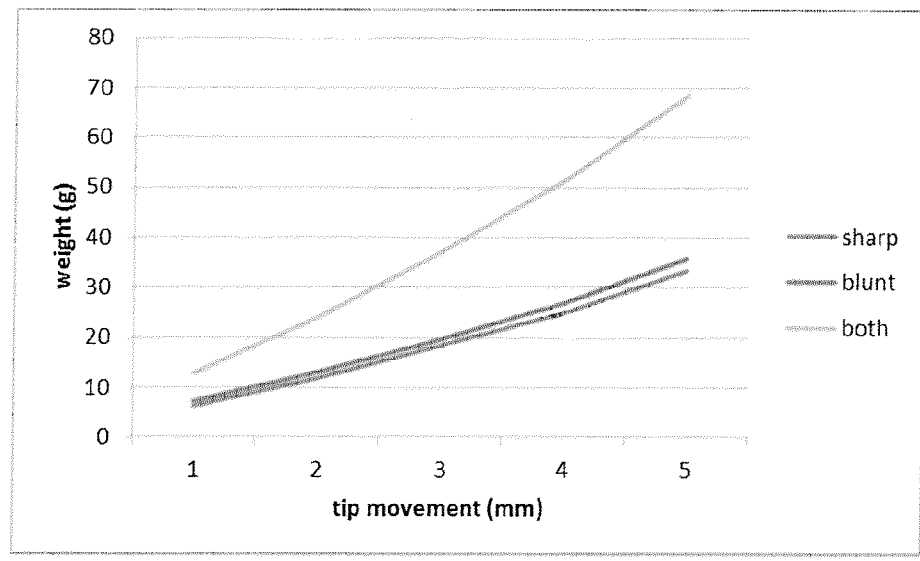

FIG. 1:
FIG. 1 shows hyaluronan.
FIG. 2:
FIG. 2 shows an aneurysmatic vein.
FIG. 3:
After skin penetration the catheter system is coaxially advanced.
FIG. 4:
The catheter system contains a hollow needle with a double or triple cut tip (4) and a transparent plastic flashback chamber (6). It may have a Luer-lock connector. Top: puncturing position; bottom: injection position (safety position). As outlined above the diameters may vary.
FIG. 5:
After puncturing the tool is advanced without harming the vessel.
FIG. 6:
Retraction and removal of needle.
FIG. 7:
Extravascular position is shown by lack of blood in the flashback chamber, or syringe aspiration.
FIG. 8:
The aqueous solution comprising between 0.1% and 3% hyaluronic acid is injected beside the vessel.
FIG. 9:
FIG. 9 shows typical ultrasound cross-section images.
FIG. 10:
FIG. 11 shows the vein being ready for endovascular treatment.
FIG. 11:
FIG. 11 shows the vein before and after treatment with the solution according to the invention. Ultrasound, cross-sectional view.
FIG. 12
FIG. 12 shows details of the catheter system. A) shows a scheme, B) a prototype (i) system connected, (ii) inner tube with cut tip, fixed outside, (iii) outer tube with smooth tip, and (ii again) of outer tube (puncturing position) and (iii again) inner tube retracted.
FIG. 13
This ultrasound image shows the groin region (saphenofemoral junction) with perivenous hyaluronan compressing the target vein during laser obliteration. The veins original diameter was 8.8 mm, and now is compressed to 2.5 mm.
FIG. 14
This ultrasound image shows the same region with hyaluronan still effective after 2 weeks. The target vein is closed. Its diameter is compressed to about 2.7 mm (mean).
FIG. 15
Experimental setup for determining preferred flexibility.
FIG. 16
Result of flexibility determination.

The invention claimed is:

1. A method for treating venous diseases characterized by dilated veins in a subject in need thereof comprising administering a composition comprising an injectable viscous aqueous solution, wherein the composition comprises about 0.1% to 3% cross-linked hyaluronic acid with a half-life within human connective tissue of more than 1 week, wherein said injectable viscous aqueous solution has a viscosity from 10 to 5000 mPa*s, and wherein said composition is administered perivascularly.

2. The method of claim 1, wherein the composition further comprises one or more of the following compounds: poly lactic acid and alginate.

3. The method of claim 1, wherein the composition is cross-linked with 1,4-butanediol diglycidyl ether (BDDE).

4. The method of claim 1, wherein the concentration of hyaluronic acid is about 0.25% to about 2%.

5. The method of claim 1, wherein the hyaluronic acid is between 1 million and 8 million Da.

6. The method of claim 2, additionally comprising a local anesthetic.

7. The method of claim 6, wherein the local anesthetic is selected from the group consisting of scandicain, mepivacaine, cocaine, procaine, benzocaine (ethoform), lidocaine, mepivacain, bupivacaine, ropivacain, etidocain, prilocain and tetracain.

8. The method of claim 1, wherein the venous disease is selected from the group consisting of aneurysm, varicose veins, insufficient veins, dilated veins and ectasias.

9. The method according to claim 1, wherein the treatment with the composition is for shaping of dilated, incompetent valve sections by reducing the diameter.

10. The method according to claim 1, wherein the composition comprises about 0.5% to 1% cross-linked hyaluronic acid.

* * * * *